(12) United States Patent
Heidelbaugh et al.

(10) Patent No.: US 8,703,746 B2
(45) Date of Patent: Apr. 22, 2014

(54) COMPOUNDS AS RECEPTOR MODULATORS WITH THERAPEUTIC UTILITY

(71) Applicant: Allergan, Inc., Irvine, CA (US)

(72) Inventors: Todd M. Heidelbaugh, Fountain Valley, CA (US); Phong X. Nguyen, Placentia, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/071,534

(22) Filed: Nov. 4, 2013

(65) Prior Publication Data

US 2014/0057876 A1 Feb. 27, 2014

Related U.S. Application Data

(63) Continuation of application No. 13/300,537, filed on Nov. 18, 2011.

(60) Provisional application No. 61/416,081, filed on Nov. 22, 2010.

(51) Int. Cl.

| | |
|---|---|
| A61K 31/67 | (2006.01) |
| A61K 31/4178 | (2006.01) |
| A61K 31/443 | (2006.01) |
| A61K 31/4439 | (2006.01) |
| A61K 31/665 | (2006.01) |
| A61K 31/675 | (2006.01) |
| A61P 1/00 | (2006.01) |
| A61P 9/10 | (2006.01) |
| A61P 11/00 | (2006.01) |
| A61P 11/06 | (2006.01) |
| A61P 17/02 | (2006.01) |
| A61P 17/06 | (2006.01) |
| A61P 17/18 | (2006.01) |
| A61P 19/02 | (2006.01) |
| A61P 19/04 | (2006.01) |
| A61P 19/08 | (2006.01) |
| A61P 19/10 | (2006.01) |
| A61P 25/00 | (2006.01) |
| A61P 25/28 | (2006.01) |
| A61P 27/02 | (2006.01) |
| A61P 27/06 | (2006.01) |
| A61P 29/00 | (2006.01) |
| A61P 35/04 | (2006.01) |
| A61P 37/00 | (2006.01) |
| A61P 37/06 | (2006.01) |
| A61P 37/08 | (2006.01) |

(52) U.S. Cl.
USPC .......................................................... 514/89

(58) Field of Classification Search
None
See application file for complete search history.

(56) References Cited

U.S. PATENT DOCUMENTS

| | | |
|---|---|---|
| 4,952,683 A | 8/1990 | Tschannen et al. |
| 5,102,901 A | 4/1992 | van Wijngaarden et al. |
| 5,110,987 A | 5/1992 | Liotta et al. |
| 5,294,722 A | 3/1994 | Kim |
| 5,403,851 A | 4/1995 | D'Orlando et al. |
| 5,580,878 A | 12/1996 | D'Orlando et al. |
| 6,235,912 B1 | 5/2001 | Takesako et al. |
| 6,239,297 B1 | 5/2001 | Takesako et al. |
| 2003/0125371 A1 | 7/2003 | Elokdah et al. |
| 2005/0080124 A1 | 4/2005 | Teegarden et al. |

FOREIGN PATENT DOCUMENTS

| | | |
|---|---|---|
| EP | 1602660 | 12/2005 |
| WO | WO2005-014525 | 2/2005 |
| WO | WO2006-068410 A1 | 6/2006 |
| WO | WO2008-016674 | 2/2008 |
| WO | WO2009-043889 | 4/2009 |
| WO | 2010-042998 | 4/2010 |
| WO | 2010-051349 | 5/2010 |

OTHER PUBLICATIONS

Cross, L.C. et al, Rules for the Nomenclature of Organic Chemistry, Section E: Stereochemistry, Pure & Appl. Chem., 1976, 11-30, 45.
Jeffrey Hale et al, Potent S1P Receptor Agonists Replicate the Pharmacologic Actions of the Novel Immune Modulator FTY720, Bioorganic & Medicinal Chemistry Letters, 2004, 3351-3355, 14 (12).
Stahl, Heinrich et al, Handbook of Pharmaceutical Salts, Verlag Helvetica Chimica Acta—Zurich, 2002, 329-345.
Astles et al., 7(7) Bioorg. & Med. Chem. Letts. 907-912 (1997).

*Primary Examiner* — Janet L Andres
*Assistant Examiner* — Timothy R Rozof
(74) *Attorney, Agent, or Firm* — Doina G. Ene

(57) ABSTRACT

The present invention relates to novel derivatives, processes for preparing them, pharmaceutical compositions containing them and their use as pharmaceuticals as modulators of sphingosine-1-phosphate receptors.

15 Claims, 1 Drawing Sheet

Lymphopenia induced by S1P1 agonists in mice: Time course (10 mg/Kg)
(2S)-2-amino-3-oxo-3-({4-[(5-phenylpentyl)oxy]-3-(2-thienyl)phenyl}amino)propyl dihydrogen phosphate
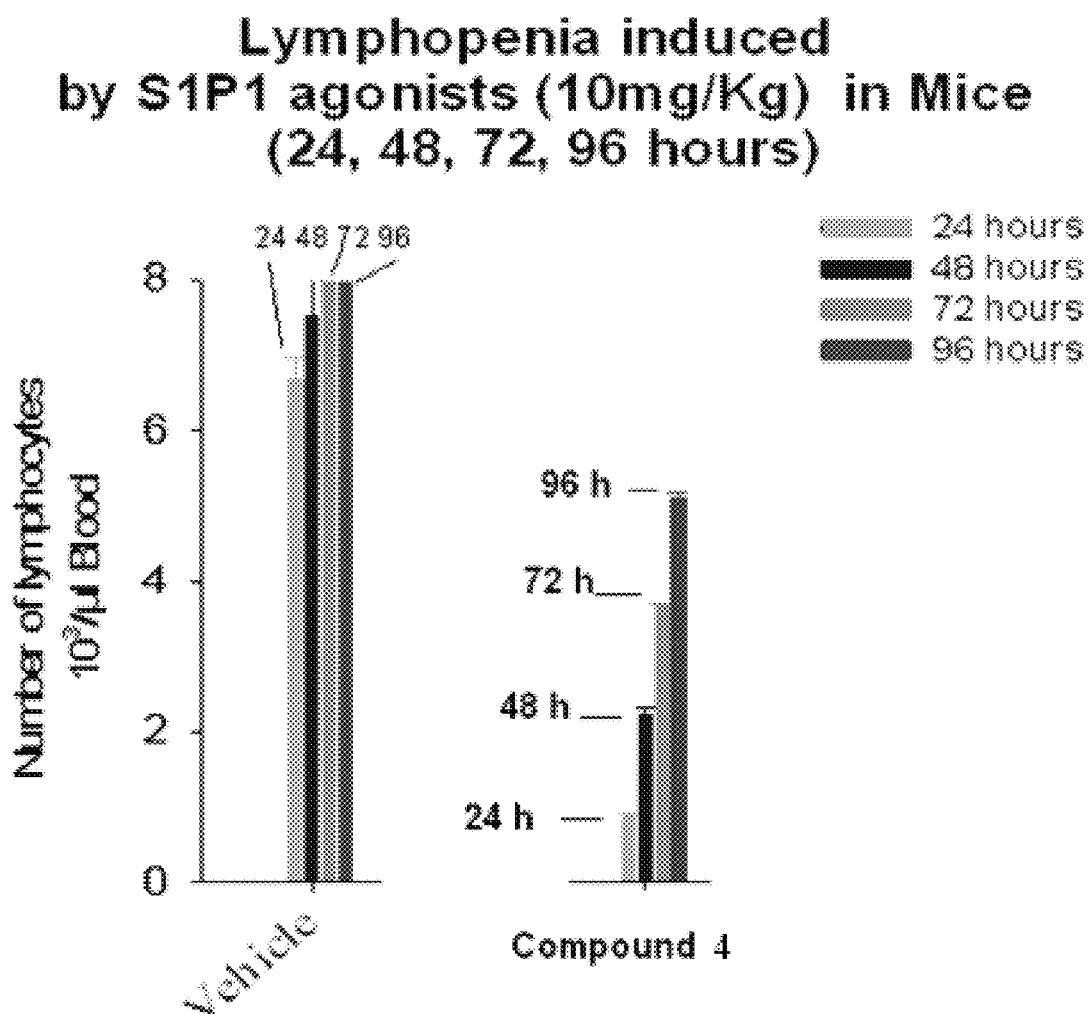

COMPOUNDS AS RECEPTOR MODULATORS WITH THERAPEUTIC UTILITY

CROSS REFERENCE TO RELATED APPLICATIONS

This application is a continuation application of U.S. Non-Provisional patent application Ser. No. 13/300,537, filed Nov. 18, 2011, which claims the benefit of U.S. Provisional Application Ser. No. 61/416,081 filed Nov. 22, 2010, which is hereby incorporated by reference in its entirety.

FIELD OF THE INVENTION

The present invention relates to novel derivatives, processes for preparing them, pharmaceutical compositions containing them and their use as pharmaceuticals, as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation. In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

In one embodiment of the invention, there are provided compounds having the Formula I below and pharmaceutically accepted salts thereof, its enantiomers, diastereoisomers, hydrates, solvates, crystal forms and individual isomers, tautomers or a pharmaceutically acceptable salt thereof, Formula I wherein:
$R^1$ is N or C—$R^9$;
$R^2$ is substituted or unsubstituted aromatic heterocycle, $C_{5-8}$ cycloalkenyl or $C_{6-10}$ aryl;
$R^3$ is O, N—$R^{10}$, CH—$R^{11}$, S, —$CR^{12}$=$CR^{13}$—, —C≡C— or —C(O)—;
$R^4$ is H, $C_{5-8}$ cycloalkenyl, $C_{3-8}$ cycloalkyl or substituted or unsubstituted $C_{6-10}$ aryl;
$R^5$ is H, halogen, —$OC_{1-3}$ alkyl, $C_{1-3}$ alkyl or hydroxyl;
$R^6$ is H, halogen, —$OC_{1-3}$ alkyl, $C_{1-3}$ alkyl or hydroxyl;
a is 0, 1, 2, 3 or 4;
b is 0, 1, 2, 3 or 4;
L is $CHR^7$, O, S, $NR^8$ or —C(O)—;
$R^7$ is H, $C_{1-3}$ alkyl, —$OC_{1-3}$ alkyl, halogen, hydroxyl or $NR^9R^{10}$;
$R^8$ is H or $C_{1-3}$ alkyl;
$R^9$ is H, halogen or $C_{1-3}$ alkyl;
$R^{10}$ is H or $C_{1-3}$ alkyl;
$R^{11}$ is H or $C_{1-3}$ alkyl;
$R^{12}$ is H or $C_{1-3}$ alkyl;
$R^{13}$ is H or $C_{1-3}$ alkyl;
$Q^1$ is —$CR^{14}R^{15}$—;
$R^{14}$ is H, halogen, or $C_{1-3}$ alkyl;
$R^{15}$ is H, halogen, or $C_{1-3}$ alkyl;
m is 0, 1, 2 or 3;

T is —NH—$Q^2$,

"*" represents the point of attachment to the rest of the molecule;

$R^{18}$ is $NR^9$, O, or S;
$Q^2$ is the same or independently —$OPO_3H_2$, carboxylic acid, —$PO_3H_2$, —$C_{1-6}$ alkyl, H, —

$S(O)_2OH$, —$P(O)MeOH$, —$P(O)(H)OH$, —OH

[chemical structures]

with the proviso that when $R^3$ is O, N—$R^{10}$, S, —$CR^{12}$=$CR^{13}$—, —C≡C— or —C(O)— and b is 0 or 1 then L is not O, S, $NR^8$ or —C(O)—.

In another aspect, the invention provides a compound having Formula I wherein:
$R^1$ is N or C—$R^9$;
$R^2$ is a five-membered aromatic substituted or unsubstituted heterocycle or $C_{5-8}$ cycloalkenyl;
$R^3$ is O, N—$R^{10}$, CH—$R^{11}$, S;
$R^4$ is substituted or unsubstituted $C_{6-10}$ aryl;
$R^5$ is H, or halogen;
$R^6$ is H or halogen;
$R^8$ is H or $C_{1-3}$ alkyl;
$R^9$ is H or $C_{1-3}$ alkyl;
$R^{10}$ is H or $C_{1-3}$ alkyl;
$R^{11}$ is H or $C_{1-3}$ alkyl;
a is 0, 1, 2, 3 or 4;
b is 0, 1, 2, 3 or 4;
L is $CH_2$;
m is 0;
T is —NH-$Q^2$;

$Q^2$ is —$C_{1-6}$ alkyl, [structures] or [structure]

"*" represents the point of attachment to the rest of the molecule.

In another aspect, the invention provides a compound having Formula I wherein:
$R^1$ is N or C—$R^9$;
$R^2$ is furan, 2-furyl and 3-furyl derivatives; thiophene, 2-thienyl and 3-thienyl derivatives; pyrrole, oxazole, thiazole, pyrrolidine, pyrroline, imidazole, pyrazole, pyrazoline, isoxazole, isothiazole, pyrazolidine, imidazoline, thiazoline, oxazoline, dihydrothiophene, dihydrofuran, tetrazole, triazole, oxadiazole, 1,2,5-oxadiazole, thiadiazole, 1,2,3-triazole, 1,2,4-triazole, pyrrolidinone, pyrrol-2(3H)-one, imidazolidin-2-one, or 1,2,4-triazol-5(4H)-one and the like 5-membered heterocyclic rings;

$R^3$ is O, N—$R^{10}$, CH—$R^{11}$, S;
$R^4$ is phenyl with ortho, meta and para substitution with groups such as: halogens fluoro, chloro and bromo; short chain alkyls methyl, ethyl, propyl, isopropyl and other, methoxy, trifluoromethoxy, trifluoromethyl and perfluorinated short chain alkyl groups;
$R^5$ is H, or halogen;
$R^6$ is H or halogen;
$R^8$ is H or $C_{1-3}$ alkyl;
$R^9$ is H or $C_{1-3}$ alkyl;
$R^{10}$ is H or $C_{1-3}$ alkyl;
$R^{11}$ is H or $C_{1-3}$ alkyl;
a is 0, 1, 2, 3 or 4;
b is 0, 1, 2, 3 or 4;
L is $CH_2$;
m is 0;
T is —NH-$Q^2$;

$Q^2$ is —$C_{1-6}$ alkyl, [structures] or [structure]

"*" represents the point of attachment to the rest of the molecule.

In another aspect, the invention provides a compound having Formula I wherein:
$R^1$ is C—$R^9$;
$R^2$ is a five-membered aromatic substituted or unsubstituted heterocycle or $C_{5-8}$ cycloalkenyl;
$R^3$ is O, N—$R^{10}$, CH—$R^{11}$, S;
$R^4$ is substituted or unsubstituted $C_{6-10}$ aryl;
$R^5$ is H, or halogen;
$R^6$ is H or halogen;
$R^8$ is H or $C_{1-3}$ alkyl;
$R^9$ is H or $C_{1-3}$ alkyl;
$R^{10}$ is H or $C_{1-3}$ alkyl;
$R^{11}$ is H or $C_{1-3}$ alkyl;
a is 0, 1, 2, 3 or 4;
b is 0, 1, 2, 3 or 4;
L is $CH_2$;
m is 0;
T is —NH-$Q^2$;

$Q^2$ is —$C_{1-6}$ alkyl, [structures] or [structure]

"*" represents the point of attachment to the rest of the molecule.

In another aspect, the invention provides a compound having Formula I wherein:
$R^1$ is C—$R^9$;
$R^2$ is a five-membered aromatic substituted or unsubstituted heterocycle;
$R^3$ is O;
$R^4$ is substituted or unsubstituted phenyl;
$R^5$ is H, Cl, Br or F;
$R^6$ is H, Cl, Br or F;
a is 1, 2, or 3;

b is 1, 2, or 3;
L is $CHR^7$;
$R^7$ is H or $C_{1-3}$ alkyl;
m is 0;
T is —NH-$Q^2$;

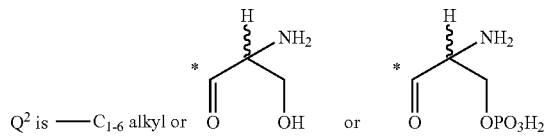

"*" represents the point of attachment to the rest of the molecule.

In another aspect, the invention provides a compound having Formula I wherein:
$R^1$ is C—$R^9$;
$R^2$ is a five-membered aromatic substituted or unsubstituted heterocycle;
$R^3$ is O;
$R^4$ is substituted or unsubstituted phenyl;
$R^5$ is H, Cl, Br or F;
$R^6$ is H, Cl, Br or F;
a is 1, 2, or 3;
b is 1, 2, or 3;
L is $CHR^7$;
$R^7$ is H or $C_{1-3}$ alkyl;
m is 0;
T is —NH-$Q^2$;

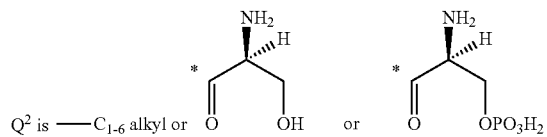

"*" represents the point of attachment to the rest of the molecule.

In another aspect, the invention provides a compound having Formula I wherein:
$R^1$ is C—$R^9$;
$R^2$ is a five-membered aromatic substituted or unsubstituted heterocycle;
$R^3$ is O;
$R^4$ is substituted or unsubstituted phenyl;
$R^5$ is H or F;
$R^6$ is H or F;
$R^8$ is H or $C_{1-3}$ alkyl;
$R^9$ is H or $C_{1-3}$ alkyl;
a is 1, 2, or 3;
b is 1, 2, or 3;
L is $CH_2$;
m is 0;
T is —NH-$Q^2$;

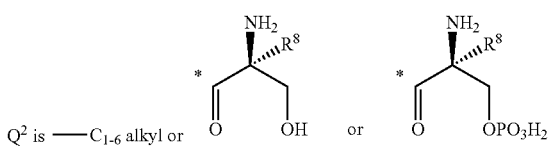

"*" represents the point of attachment to the rest of the molecule.

In another aspect, the invention provides a compound having Formula I wherein:
$R^1$ is C—$R^9$;
$R^2$ is a five-membered aromatic substituted or unsubstituted heterocycle;
$R^3$ is O;
$R^4$ is substituted or unsubstituted phenyl;
$R^5$ is H or F;
$R^6$ is H or F;
$R^9$ is H;
a is 2;
b is 2;
L is $CH_2$;
m is 0;
T is —NH-$Q^2$;
$Q^2$ is —$C_{1-6}$ alkyl,

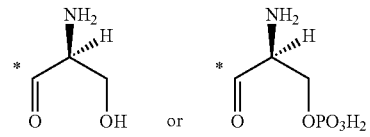

"*" represents the point of attachment to the rest of the molecule.

In another aspect, the invention provides a compound having Formula I wherein:
$R^1$ is C—$R^9$ or N;
$R^2$ is a five-membered aromatic substituted or unsubstituted heterocycle;
$R^3$ is O;
$R^4$ is substituted or unsubstituted $C_{6-10}$ aryl;
a is 0, 1, 2, 3 or 4;
b is 0, 1, 2, 3 or 4;
$R^5$ is H, or F,
$R^6$ is H, or F,
$R^9$ is H or $C_{1-3}$ alkyl;
L is $CH_2$;
$Q^1$ is —$CR^{14}R^{15}$—;
$R^{14}$ is H;
$R^{15}$ is H;
m is 2;

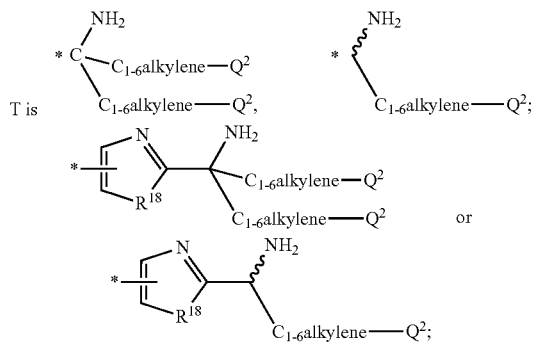

"*" represents the point of attachment to the rest of the molecule;
$R^{18}$ is $NR^9$;
$Q^2$ is —$OPO_3H_2$, —OH, carboxylic acid, —$PO_3H_2$, H, —$C_{1-6}$ alkyl, —P(O)MeOH or —P(O)(H)OH.

In another aspect, the invention provides a compound having Formula I wherein:
$R^1$ is C—$R^9$ or N;
$R^2$ is a five-membered substituted or unsubstituted heterocycle;
$R^3$ is O;
$R^4$ is substituted or unsubstituted phenyl;
$R^5$ is H, or F;
$R^6$ is H or F;
a is 1, 2, or 3;
b is 1, 2, or 3;
$R^9$ is H or $C_{1-3}$ alkyl;
L is $CH_2$;
$Q^1$ is —$CR^{14}R^{15}$—;
$R^{14}$ is H;
$R^{15}$ is H;
m is 2;

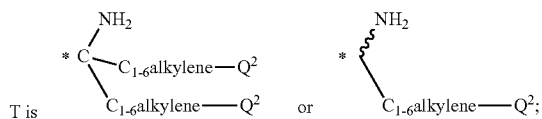

"*" represents the point of attachment to the rest of the molecule;
$Q^2$ is —$OPO_3H_2$, —OH, carboxylic acid, —$PO_3H_2$, H, —$C_{1-6}$ alkyl, —P(O)MeOH or —P(O)(H)OH.

In another aspect, the invention provides a compound having Formula I wherein:
$R^1$ is C—$R^9$;
$R^2$ is a five-membered aromatic substituted or unsubstituted heterocycle;
$R^3$ is O;
$R^4$ is substituted or unsubstituted phenyl;
$R^5$ is H or F;
$R^6$ is H or F;
$R^9$ is H;
a is 2;
b is 2;
L is $CH_2$;
$Q^1$ is —$CR^{14}R^{15}$—;
$R^{14}$ is H;
$R^{15}$ is H;
m is 2;

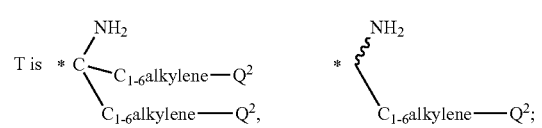

"*" represents the point of attachment to the rest of the molecule;
$Q^2$ is —$OPO_3H_2$, —OH, carboxylic acid, —$PO_3H_2$, H, —$C_{1-6}$ alkyl, —P(O)MeOH or —P(O)(H)OH.

In another aspect, the invention provides a compound having Formula I wherein:
$R^1$ is N or C—$R^9$;
$R^2$ is a five-membered aromatic substituted or unsubstituted heterocycle;
$R^3$ is O;
$R^4$ is substituted or unsubstituted phenyl;
$R^5$ is H, or F;
$R^6$ is H, or F;
a is 1, 2, or 3;
b is 1, 2, or 3;
L is $CH_2$;
$R^9$ is H or $C_{1-3}$ alkyl;
m is 0;

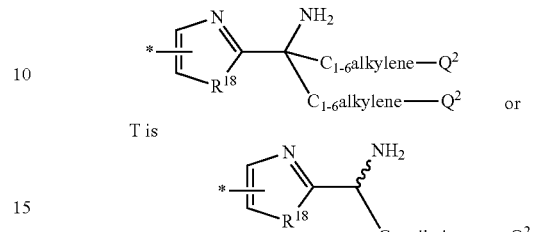

"*" represents the point of attachment to the rest of the molecule;
$R^{18}$ is $NR^9$;
$Q^2$ is —$OPO_3H_2$, —OH, carboxylic acid, —$PO_3H_2$, H, —$C_{1-6}$ alkyl, —P(O)MeOH or —P(O)(H)OH.

In another aspect, the invention provides a compound having Formula I wherein:
$R^1$ is C—$R^9$
$R^2$ is a five-membered aromatic substituted or unsubstituted heterocycle;
$R^3$ is O;
$R^4$ is substituted or unsubstituted phenyl;
$R^5$ is H, or F;
$R^6$ is H, or F;
$R^9$ is H;
a is 2;
b is 2;
L is $CH_2$;
m is 0;

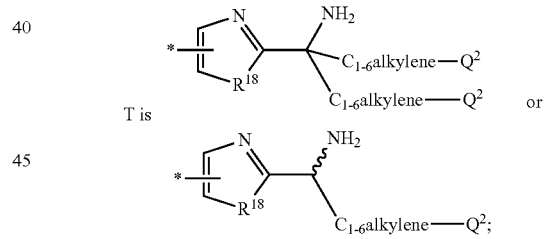

"*" represents the point of attachment to the rest of the molecule;
$R^{18}$ is $NR^9$;
$Q^2$ is —$OPO_3H_2$, —OH, carboxylic acid, —$PO_3H_2$, H, —$C_{1-6}$ alkyl, —P(O)MeOH or —P(O)(H)OH.

In another aspect, the invention provides a compound having Formula I wherein:
$R^1$ is N or C—$R^9$;
$R^2$ is substituted or unsubstituted heterocycle, $C_{6-8}$ cycloalkenyl or $C_{6-10}$ aryl;
$R^3$ is O, N—$R^{10}$, CH—$R^{11}$, S, —$CR^{12}$=$CR^{13}$—, —C≡C— or —C(O)—;
$R^4$ is H, $C_{6-8}$ cycloalkenyl, $C_{3-8}$ cycloalkyl or substituted or unsubstituted $C_{6-10}$ aryl;
$R^5$ is H, halogen, —$OC_{1-3}$ alkyl, $C_{1-3}$ alkyl or hydroxyl;
$R^6$ is H, halogen, —$OC_{1-3}$ alkyl, $C_{1-3}$ alkyl or hydroxyl;
a is 0, 1, 2, 3 or 4;
b is 0, 1, 2, 3 or 4;

L is $CHR^7$, O, S, $NR^8$ or —C(O)—;
$R^7$ is H, $C_{1-3}$ alkyl, —$OC_{1-3}$ alkyl, halogen, hydroxyl or $NR^9R^{10}$;
$R^8$ is H or $C_{1-3}$ alkyl;
$R^9$ is H, halogen or $C_{1-3}$ alkyl;
$R^{10}$ is H or $C_{1-3}$ alkyl;
$R^{11}$ is H or $C_{1-3}$ alkyl;
$R^{12}$ is H or $C_{1-3}$ alkyl;
$R^{13}$ is H or $C_{1-3}$ alkyl;
$Q^1$ is —$CR^{14}R^{15}$—;
$R^{14}$ is H, halogen, or $C_{1-3}$ alkyl;
$R^{15}$ is H, halogen, or $C_{1-3}$ alkyl;
m is 0, 1, 2 or 3;

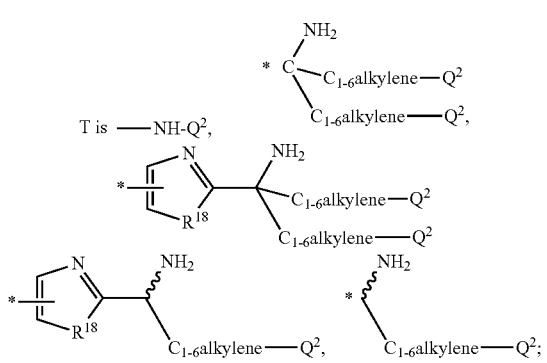

"*" represents the point of attachment to the rest of the molecule;
$R^{18}$ is $NR^9$, O, or S;
$Q^2$ is the same or independently —$OPO_3H_2$, carboxylic acid, —$PO_3H_2$, —$C_{1-6}$ alkyl, H, —$S(O)_2OH$, —P(O)MeOH, —P(O)(H)OH, —OH

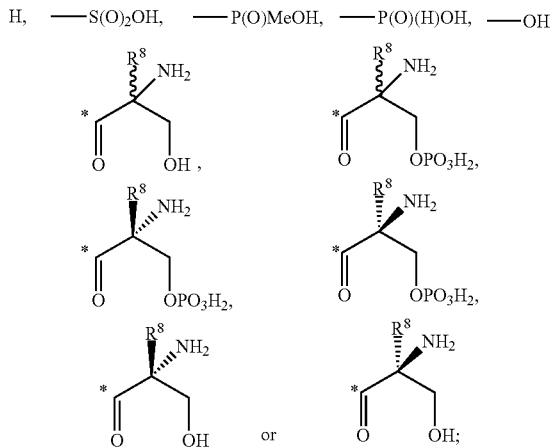

with the proviso that when $R^3$ is O, N—$R^{10}$, S, —$CR^{12}$=$CR^{13}$—, —C≡C— or —C(O)— and b is 0 or 1 then L is not O, S, $NR^8$ or —C(O)—.

In another aspect, the invention provides a compound having Formula I wherein:
$R^1$ is C—$R^9$;
$R^2$ is a five-membered substituted or unsubstituted heterocycle;
$R^3$ is O;
$R^4$ is substituted or unsubstituted $C_{6-10}$ aryl;
$R^5$ is H or halogen;
$R^6$ is H or halogen;
a is 1 or 2;
b is 1 or 2;
L is $CHR^7$;
$R^7$ is H;
$R^9$ is H or $C_{1-3}$ alkyl;
$Q^1$ is —$CR^{14}R^{15}$—;
$R^{14}$ is H;
$R^{15}$ is H;
m is 2;

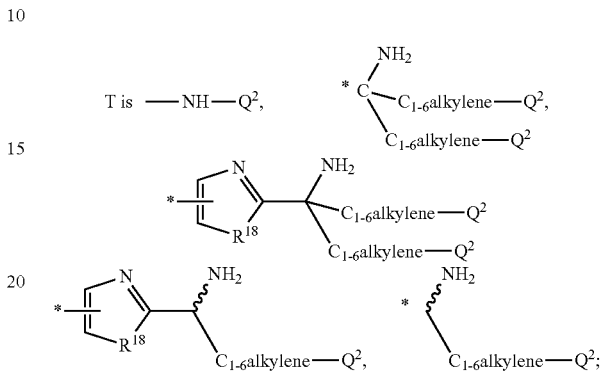

"*" represents the point of attachment to the rest of the molecule;
$R^{18}$ is $NR^9$;
$Q^2$ is the same or independently —$OPO_3H_2$, carboxylic acid, —$PO_3H_2$, —$C_{1-6}$ alkyl, H, —P(O)MeOH, —P(O)(H)OH, —OH.

In another aspect, the invention provides a compound having Formula I wherein:
$R^1$ is C—$R^9$;
$R^2$ is a five-membered substituted or unsubstituted heterocycle;
$R^3$ is O;
$R^4$ is substituted or unsubstituted $C_{6-10}$ aryl;
$R^5$ is H or halogen;
$R^6$ is H or halogen;
a is 1 or 2;
b is 1 or 2;
L is $CHR^7$;
$R^7$ is H;
$R^9$ is H or $C_{1-3}$ alkyl;
$Q^1$ is —$CR^{14}R^{15}$—;
$R^{14}$ is H;
$R^{15}$ is H;
m is 2;
T is —NH-$Q^2$,

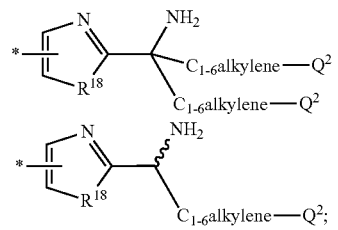

"*" represents the point of attachment to the rest of the molecule;
$R^{18}$ is $NR^9$;
$Q^2$ is the same or independently —$OPO_3H_2$, carboxylic acid, —$PO_3H_2$, —$C_{1-6}$ alkyl, H, —P(O)MeOH, —P(O)(H)OH, —OH.

In another aspect, the invention provides a compound having Formula I wherein:
$R^1$ is C—$R^9$;
$R^2$ is a five-membered substituted or unsubstituted heterocycle;
$R^3$ is O;
$R^4$ is substituted or unsubstituted $C_{6-10}$ aryl;
$R^5$ is H or halogen;
$R^6$ is H or halogen;
a is 1 or 2;
b is 1 or 2;
L is $CHR^7$;
$R^7$ is H;
$R^9$ is H or $C_{1-3}$ alkyl;
$Q^1$ is —$CR^{14}R^{15}$—;
$R^{14}$ is H;
$R^{15}$ is H;
m is 2;

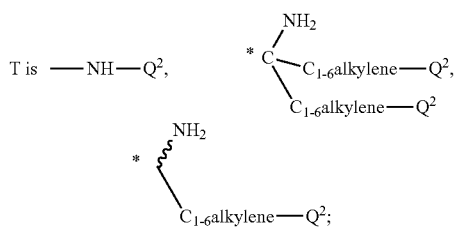

"*" represents the point of attachment to the rest of the molecule;
$Q^2$ is the same or independently —$OPO_3H_2$, carboxylic acid, —$PO_3H_2$, —$C_{1-6}$ alkyl, H, —P(O)MeOH, —P(O)(H)OH, —OH.

In another aspect, the invention provides a compound having Formula I wherein:
$R^1$ is C—$R^9$;
$R^2$ is substituted or unsubstituted heterocycle;
$R^3$ is O;
$R^4$ is substituted or unsubstituted phenyl;
$R^5$ is H or halogen;
$R^6$ is H or halogen;
a is 2;
b is 2;
L is $CHR^7$;
$R^7$ is H;
$R^9$ is H;
m is 0;
T is —NH-$Q^2$,
"*" represents the point of attachment to the rest of the molecule;
$Q^2$ is the same or independently —$OPO_3H_2$, carboxylic acid, —$PO_3H_2$, —$C_{1-6}$ alkyl, H, —$S(O)_2OH$, —P(O)MeOH, —P(O)(H)OH, —OH

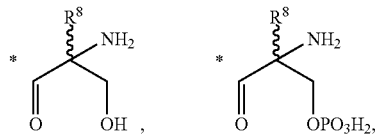

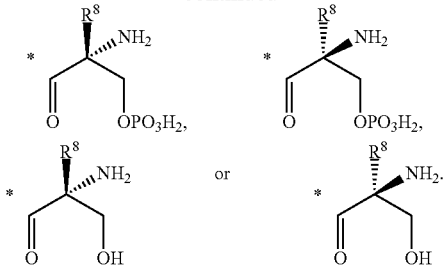

In another aspect, the invention provides a compound having Formula I wherein:
$R^1$ is C—$R^9$;
$R^2$ is substituted or unsubstituted heterocycle;
$R^3$ is O;
$R^4$ is substituted or unsubstituted phenyl;
$R^5$ is H or halogen;
$R^6$ is H or halogen;
a is 2;
b is 2;
L is $CHR^7$;
$R^7$ is H;
$R^9$ is H;
m is 0;
T is —NH-$Q^2$,
"*" represents the point of attachment to the rest of the molecule;
$Q^2$ is the same or independently —$OPO_3H_2$, carboxylic acid, —$PO_3H_2$, —$C_{1-6}$ alkyl, H, —$S(O)_2OH$, —P(O)MeOH, —P(O)(H)OH, —OH

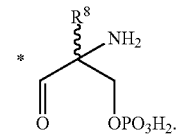

In another aspect, the invention provides a compound having Formula I wherein:
$R^1$ is C—$R^9$;
$R^2$ is substituted or unsubstituted heterocycle;
$R^3$ is O;
$R^4$ is substituted or unsubstituted phenyl;
$R^5$ is H or halogen;
$R^6$ is H or halogen;
a is 2;
b is 2;
L is $CHR^7$;
$R^7$ is H;
$R^9$ is H;
m is 0;
T is —NH-$Q^2$,
"*" represents the point of attachment to the rest of the molecule;
$Q^2$ is the same or independently —$OPO_3H_2$, carboxylic acid, —$PO_3H_2$, —$C_{1-6}$ alkyl, H, —S(O)₂OH, —P(O)MeOH, —P(O)(H)OH, —OH

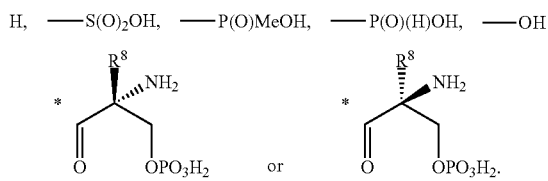

In another aspect, the invention provides a compound having Formula I wherein:

$R^1$ is C—$R^9$;
$R^2$ is substituted or unsubstituted heterocycle;
$R^3$ is O;
$R^4$ is substituted or unsubstituted phenyl;
$R^5$ is H or halogen;
$R^6$ is H or halogen;
a is 2;
b is 2;
L is CH$R^7$;
$R^7$ is H;
$R^9$ is H;
m is 0;
T is —NH-$Q^2$,
 "*" represents the point of attachment to the rest of the molecule;
$Q^2$ is the same or independently —OPO$_3$H$_2$, carboxylic acid, —PO$_3$H$_2$, —C$_{1-6}$ alkyl, H, —S(O)₂OH, —P(O)MeOH, —P(O)(H)OH, —OH

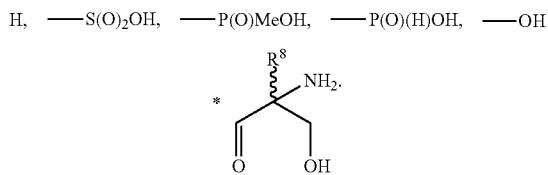

In another aspect, the invention provides a compound having Formula I wherein:

$R^1$ is C—$R^9$;
$R^2$ is substituted or unsubstituted heterocycle;
$R^3$ is O;
$R^4$ is substituted or unsubstituted phenyl;
$R^5$ is H or halogen;
$R^6$ is H or halogen;
a is 2;
b is 2;
L is CH$R^7$;
$R^7$ is H;
$R^9$ is H;
m is 0;
T is —NH-$Q^2$,
 "*" represents the point of attachment to the rest of the molecule;
$Q^2$ is the same or independently —OPO$_3$H$_2$, carboxylic acid, —PO$_3$H$_2$, —C$_{1-6}$ alkyl, H, —S(O)₂OH, —P(O)MeOH, —P(O)(H)OH, —OH,

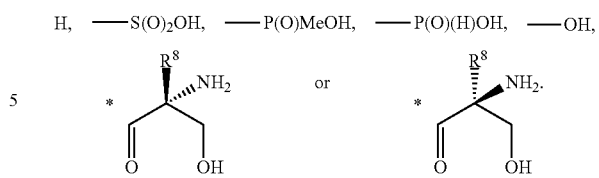

The term "alkyl", as used herein, refers to saturated, monovalent hydrocarbon moieties having linear or branched moieties or combinations thereof and containing 1 to 6 carbon atoms. One methylene (—CH$_2$—) group, of the alkyl can be replaced by oxygen, sulfur, sulfoxide, nitrogen, carbonyl, carboxyl, sulfonyl, or by a divalent C$_{3-6}$ cycloalkyl. Alkyl groups can be substituted by halogen, amino, hydroxyl, cycloalkyl, amino, non-aromatic heterocycles, carboxylic acid, phosphonic acid groups, sulphonic acid groups, phosphoric acid.

The term "short chain alkyl" as used herein, refers to saturated monovalent linear or branched moieties containing 1 to 3 carbon atoms.

The term perfluorinated short chain alkyl groups as used herein, refers to but CF$_3$—CF$_2$—, CF$_3$, (CF$_3$)$_2$—CH—, CF$_3$—(CF$_3$)$_2$—.

The term "alkylene", as used herein, refers to saturated, divalent hydrocarbon moieties having linear or branched moieties or combinations thereof and containing 1 to 6 carbon atoms. One methylene (—CH$_2$—) group of the alkylene can be replaced by oxygen, sulfur, sulfoxide, nitrogen, carbonyl, carboxyl, sulfonyl.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by 1 to 3 C$_{1-3}$ alkyl groups or 1 or 2 halogens.

The term "cycloalkenyl", as used herein, refers to a monovalent or divalent group of 5 to 8 carbon atoms, derived from a saturated cycloalkyl having one double bond. Cycloalkenyl groups can be monocyclic or polycyclic. Cycloalkenyl groups can be substituted by C$_{1-3}$ alkyl groups or halogens.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. C$_{2-6}$ alkenyl can be in the E or Z configuration. Alkenyl groups can be substituted by C$_{1-3}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which is aromatic or non-aromatic, saturated or non-saturated and containing at least one heteroatom selected form O or N or S or combinations of at least two thereof, interrupting the carbocyclic ring structure. The heterocyclic ring can be interrupted by a C═O; the S heteroatom can be oxidized. Heterocycles can be monocyclic or polycyclic. Heterocyclic ring moieties can be substituted by hydroxyl, C$_{1-3}$ alkyl or halogens. Examples of aromatic heterocycles are, but not limited to: furan, 2-furyl and 3-furyl derivatives; thiophene, 2-thienyl, 3-thienyl derivatives; pyrrole, oxazole, thiazole, imidazole, pyrazole, isoxazole, isothiazole, tetrazole, triazole, oxadiazole, 1,2,5-oxadiazole, thiadiazole, 1,2,3-triazole, 1,2,4-triazole.

Examples of non-aromatic heterocycles are, but not limited to: pyrrolidine, pyrroline, pyrazoline, pyrazolidine, imidazoline, thiazoline, oxazoline, dihydrothiophene, dihydrofuran, pyrrolidinone, pyrrol-2(3H)-one, imidazolidin-2-one, or 1,2,4-triazol-5(4H)-one.

Usually, in the present case, heterocyclic groups are 5 or 6 membered rings including but not limited to: 1-substituted-1H-1,2,4-triazole, 1-substituted-azetidine-3-$CO_2H$, 4-linked-indole, 6-methyl-5-linked-indazole or 6-hydro-5-linked-indazole. Some preferred heterocycles at the $R^2$ position include the following: furan, 2-furyl and 3-furyl derivatives; thiophene, 2-thienyl and 3-thienyl derivatives; pyrrole, oxazole, thiazole, pyrrolidine, pyrroline, imidazole, pyrazole, pyrazoline, isoxazole, isothiazole, pyrazolidine, imidazoline, thiazoline, oxazoline, dihydrothiophene, dihydrofuran, tetrazole, triazole, oxadiazole, 1,2,5-oxadiazole, thiadiazole, 1,2,3-triazole, 1,2,4-triazole, pyrrolidinone, pyrrol-2(3H)-one, imidazolidin-2-one, or 1,2,4-triazol-5(4H)-one and the like 5-membered heterocyclic rings.

The term "aryl" as used herein, refers to an organic moiety derived from an aromatic hydrocarbon consisting of a ring containing 6 to 10 carbon atoms by removal of one hydrogen. Aryl is optionally substituted by halogen atoms or by $C_{1-3}$ alkyl groups. Preferred aryl groups at the $R^4$ position include: phenyl with ortho, meta and para substitution with groups such as: halogens fluoro, chloro and bromo; short chain alkyls methyl, ethyl, propyl, isopropyl and other, methoxy, trifluoromethoxy, trifluoromethyl and perfluorinated short chain alkyl groups.

The group of formula "—$CR^{12}$=$CR^{13}$—", as used herein, represents an alkenyl radical.

The group of formula "—C≡C—", as used herein, represents an alkynyl radical.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—$S(O)_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—$P(O)(OH)_2$".

The term "phosphoric acid" as used herein, represents a group of formula "—$(O)P(O)(OH)_2$".

The term "boronic acid", as used herein, represents a group of formula "—$B(OH)_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:
(2R)-2-amino-2-methyl-3-oxo-3-({4-[(5-phenylpentyl)oxy]-3-(2-thienyl)phenyl}amino)propyl dihydrogen phosphate;
(2S)-2-amino-2-methyl-3-oxo-3-({4-[(5-phenylpentyl)oxy]-3-(2-thienyl)phenyl}amino)propyl dihydrogen phosphate;
2-amino-3-hydroxy-2-methyl-N-{4-[(5-phenylpentyl)oxy]-3-(2-thienyl)phenyl}propanamide;
2-amino-3-hydroxy-2-methyl-N-{4-[(5-phenylpentyl)oxy]-3-(2-thienyl)phenyl}propanamide;
(2S)-2-amino-3-({3-(2-furyl)-4-[(5-phenylpentyl)oxy]phenyl}amino)-3-oxopropyl dihydrogen phosphate;
(2S)-2-amino-3-oxo-3-({4-[(5-phenylpentyl)oxy]-3-(2-thienyl)phenyl}amino)propyl dihydrogen phosphate;
2-amino-N-{3-(2-furyl)-4-[(5-phenylpentyl)oxy]phenyl}-3-hydroxypropanamide;
2-amino-3-hydroxy-N-{4-[(5-phenylpentyl)oxy]-3-(2-thienyl)phenyl}propanamide;
2-amino-3-({3-(5-fluoro-2-furyl)-4-[(5-phenylpentyl)oxy]phenyl}amino)-3-oxopropyl dihydrogen phosphate;
2-amino-3-{[4-{[5-(4-fluorophenyl)pentyl]oxy}-3-(2-furyl)phenyl]amino}-3-oxopropyl dihydrogen phosphate;
2-amino-3-({3-(3-furyl)-4-[(5-phenylpentyl)oxy]phenyl}amino)-3-oxopropyl dihydrogen phosphate;
2-amino-3-oxo-3-({4-[(5-phenylpentyl)oxy]-3-(3-thienyl)phenyl}amino)propyl dihydrogen phosphate;
2-amino-3-({6-(2-furyl)-5-[(5-phenylpentyl)oxy]pyridin-2-yl}amino)-3-oxopropyl dihydrogen phosphate;
2-amino-N-{3-(5-fluoro-2-furyl)-4-[(5-phenylpentyl)oxy]phenyl}-3-hydroxypropanamide;
2-amino-N-{3-(5-fluoro-2-furyl)-4-[(5-phenylpentyl)oxy]phenyl}-3-hydroxypropanamide;
2-amino-N-{3-(3-furyl)-4-[(5-phenylpentyl)oxy]phenyl}-3-hydroxypropanamide;
2-amino-3-hydroxy-N-{4-[(5-phenylpentyl)oxy]-3-(3-thienyl)phenyl}propanamide;
2-amino-N-{6-(2-furyl)-5-[(5-phenylpentyl)oxy]pyridin-2-yl}-3-hydroxypropanamide;
2-amino-4-{3-(2-furyl)-4-[(5-phenylpentyl)oxy]phenyl}-2-(hydroxymethyl)butyl dihydrogen phosphate;
2-amino-2-(hydroxymethyl)-4-{4-[(5-phenylpentyl)oxy]-3-(2-thienyl)phenyl}butyl dihydrogen phosphate;
2-amino-4-{3-(5-fluoro-2-furyl)-4-[(5-phenylpentyl)oxy]phenyl}-2-(hydroxymethyl)butyl dihydrogen phosphate;
2-amino-4-[4-{[5-(4-fluorophenyl)pentyl]oxy}-3-(2-furyl)phenyl]-2-(hydroxymethyl)butyl dihydrogen phosphate;
2-amino-4-{3-(3-furyl)-4-[(5-phenylpentyl)oxy]phenyl}-2-(hydroxymethyl)butyl dihydrogen phosphate;
2-amino-2-(hydroxymethyl)-4-{4-[(5-phenylpentyl)oxy]-3-(3-thienyl)phenyl}butyl dihydrogen phosphate;
2-amino-4-{6-(2-furyl)-5-[(5-phenylpentyl)oxy]pyridin-2-yl}-2-(hydroxymethyl)butyl dihydrogen phosphate;
2-amino-2-(2-{3-(2-furyl)-4-[(5-phenylpentyl)oxy]phenyl}ethyl)propane-1,3-diol;
2-amino-2-(2-{4-[(5-phenylpentyl)oxy]-3-(2-thienyl)phenyl}ethyl)propane-1,3-diol;
2-amino-2-(2-{3-(5-fluoro-2-furyl)-4-[(5-phenylpentyl)oxy]phenyl}ethyl)propane-1,3-diol;
2-amino-2-{2-[4-{[5-(4-fluorophenyl)pentyl]oxy}-3-(2-furyl)phenyl]ethyl}propane-1,3-diol;
2-amino-2-(2-{3-(3-furyl)-4-[(5-phenylpentyl)oxy]phenyl}ethyl)propane-1,3-diol;
2-amino-2-(2-{4-[(5-phenylpentyl)oxy]-3-(3-thienyl)phenyl}ethyl)propane-1,3-diol;
2-amino-2-(2-{6-(2-furyl)-5-[(5-phenylpentyl)oxy]pyridin-2-yl}ethyl)propane-1,3-diol;
2-amino-2-(4-{3-(2-furyl)-4-[(5-phenylpentyl)oxy]phenyl}-1H-imidazol-2-yl)ethyl dihydrogen phosphate;
2-amino-2-(4-{4-[(5-phenylpentyl)oxy]-3-(2-thienyl)phenyl}-1H-imidazol-2-yl)ethyl dihydrogen phosphate;

2-amino-2-(4-{3-(5-fluoro-2-furyl)-4-[(5-phenylpentyl) oxy]phenyl}-1H-imidazol-2-yl)ethyl dihydrogen phosphate;

2-amino-2-{4-[4-{[5-(4-fluorophenyl)pentyl]oxy}-3-(2-furyl)phenyl]-1H-imidazol-2-yl}ethyl dihydrogen phosphate;

2-amino-2-(4-{3-(3-furyl)-4-[(5-phenylpentyl)oxy]phenyl}-1H-imidazol-2-yl)ethyl dihydrogen phosphate;

2-amino-2-(4-{4-[(5-phenylpentyl)oxy]-3-(3-thienyl)phenyl}-1H-imidazol-2-yl)ethyl dihydrogen phosphate;

2-amino-2-(4-{6-(2-furyl)-5-[(5-phenylpentyl)oxy]pyridin-2-yl}-1H-imidazol-2-yl)ethyl dihydrogen phosphate;

2-amino-2-(4-{3-(2-furyl)-4-[(5-phenylpentyl)oxy]phenyl}-1H-imidazol-2-yl)ethanol;

2-amino-2-(4-{4-[(5-phenylpentyl)oxy]-3-(2-thienyl)phenyl}-1H-imidazol-2-yl)ethanol;

2-amino-2-(4-{3-(5-fluoro-2-furyl)-4-[(5-phenylpentyl) oxy]phenyl}-1H-imidazol-2-yl)ethanol;

2-amino-2-{4-[4-{[5-(4-fluorophenyl)pentyl]oxy}-3-(2-furyl)phenyl]-1H-imidazol-2-yl}ethanol;

2-amino-2-(4-{3-(3-furyl)-4-[(5-phenylpentyl)oxy]phenyl}-1H-imidazol-2-yl)ethanol;

2-amino-2-(4-{4-[(5-phenylpentyl)oxy]-3-(3-thienyl)phenyl}-1H-imidazol-2-yl)ethanol;

2-amino-2-(4-{6-(2-furyl)-5-[(5-phenylpentyl)oxy]pyridin-2-yl}-1H-imidazol-2-yl)ethanol.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, a hydrohalic acid, such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal& Camille G. Wermuth (Eds), Verlag Helvetica Chemica Acta—Zurich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically. Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermitits, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or antinociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant; inflammatory skin diseases, scleroderma, dermatomyositis, atopic dermatitis, lupus erythematosus, epidermolysis bullosa, and bullous pemphigold. Topical use of S1P (sphingosine) compounds is of use in the treatment of various acne diseases, acne vulgaris, and rosacea.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant; inflammatory skin diseases, scleroderma, dermatomyositis, atopic dermatitis, lupus erythematosus, epidermolysis bullosa, and bullous pemphigold.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made. Those skilled in the art will be able to routinely modify and/or adapt the following schemes to synthesize any compounds of the invention covered by Formula I.

In Scheme 1, aryl amines or aryl amine derivatives or precursors react with functionalized compounds such as halogenated or hydroxylated compounds in the presence of reagents that promote alkylation as known to synthetic chemists to give the corresponding ether intermediate. This intermediate from the last step is coupled with the boronic acid or the stannate, generally involving a metal catalyst under appropriate conditions with an R² group to give the corresponding intermediate. The previous intermediate from the coupling procedure may be converted to an aryl amine as required for the next step by deprotection or reduction methods. The intermediate from the previous step reacts to form an amide under conditions that may employ carboxylic acids and the like to give an intermediate of Formula I. This intermediate from the last step is reacted with appropriate reagents to promote phosphorylation and yield a derivative of Formula I as a Compound of the invention upon removal of any required protecting groups.

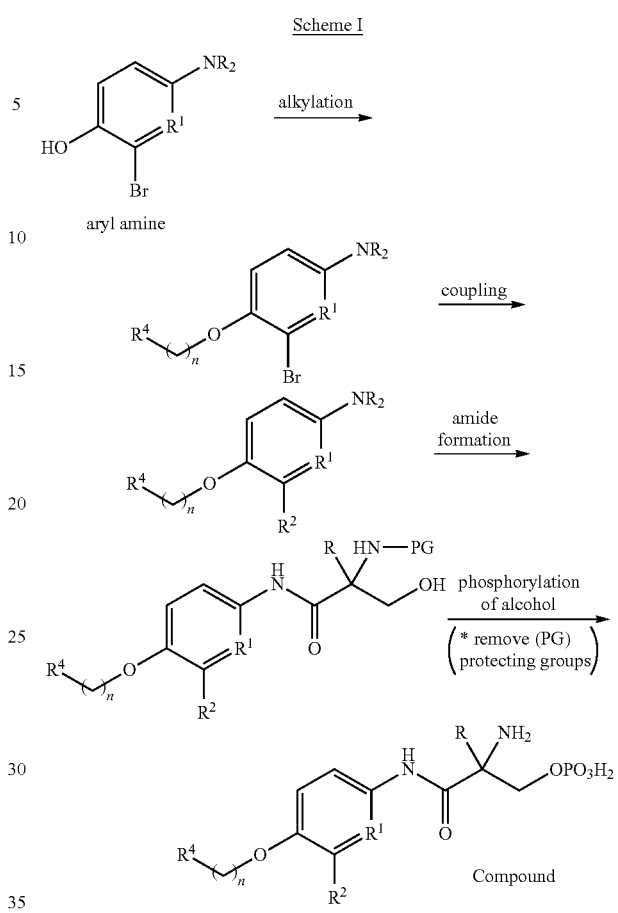

Scheme I

In Scheme II, aryl amines/amine precursors that may contain a halogen such as a bromine atom, react with functionalized compounds such as a halogenated or hydroxylated compound, in the presence of reagents that promote alkylation well known to synthetic chemists to give the corresponding ether intermediate. This intermediate from the last step is coupled with the boronic acid or the stannate involving a metal catalyst under appropriate conditions with an R² group (shown as a 2-furyl derivative below) to give the corresponding intermediate. The intermediate from the previous step may be converted to an aryl amine as required for the next step by deprotection or reduction methods. This aryl amine from the last step reacts to form an amide under conditions that may employ carboxylic acids and the like to give an intermediate of Formula I. This intermediate is reacted with appropriate reagents to promote phosphorylation and yield a derivative of Formula I as a Compound of the invention upon removal of any required protecting groups.

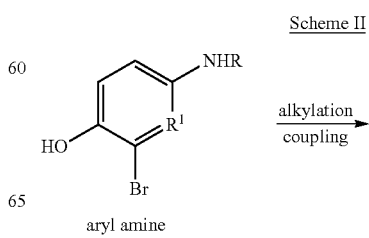

Scheme II

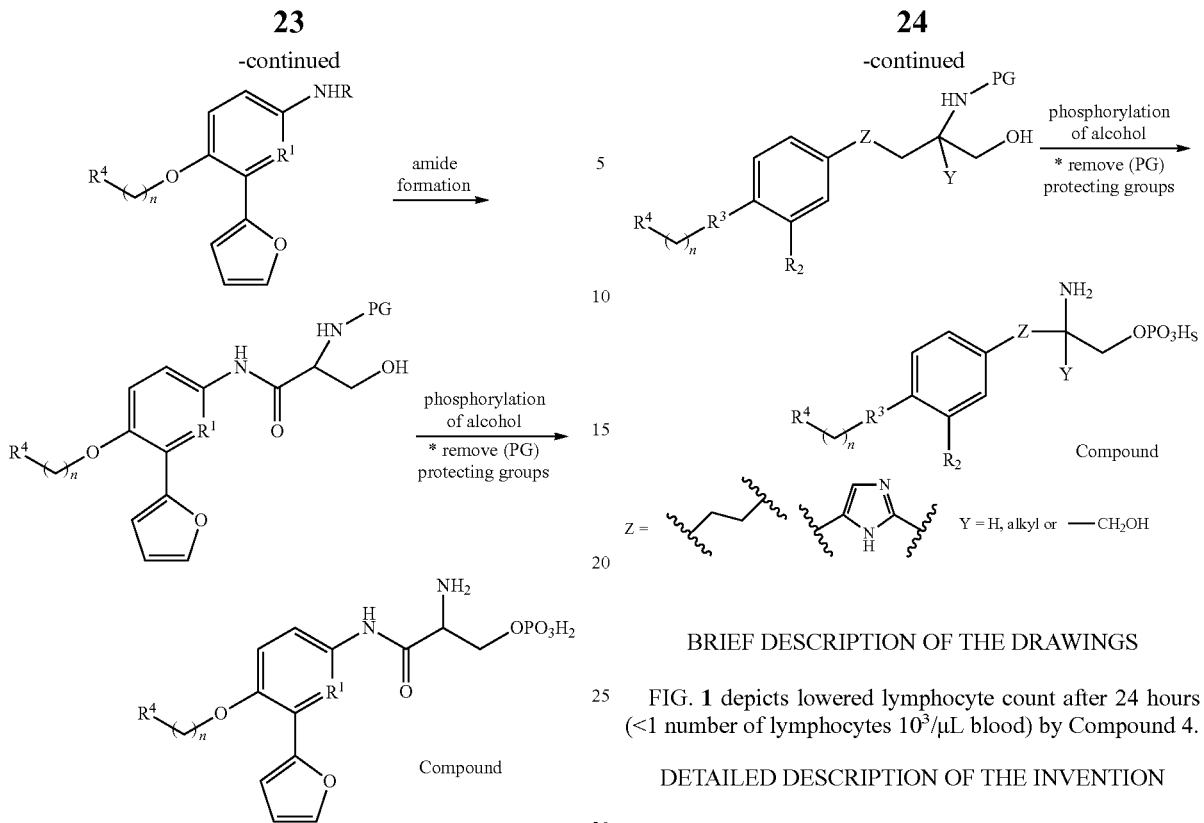

In Scheme III, elaborated aryl bromides, are obtained according to application of appropriate synthetic preparation, may react with compounds in the presence of reagents that promote alkylation. This intermediate from the last step that contains the $R^3$ group (representing an —O—, —S—, —NH—, —CH$_2$—) or other group is coupled with the boronic acid or the stannate under appropriate conditions with an $R^2$ group to give the corresponding intermediate. This intermediate from the previous step is reacted with appropriate reagents to promote phosphorylation and yield a derivative of Formula I as a Compound of the invention upon removal of any required protecting groups.

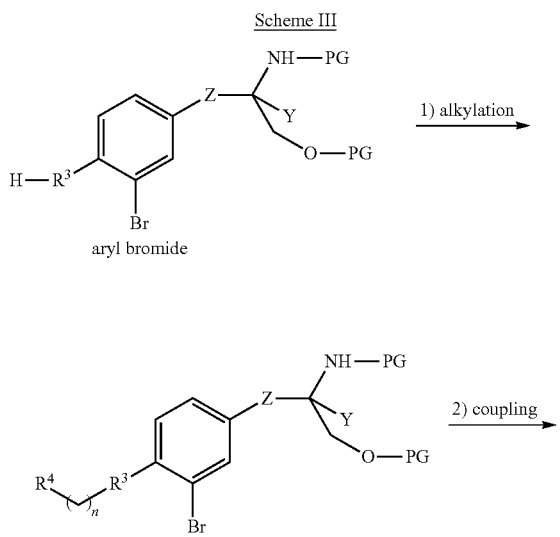

BRIEF DESCRIPTION OF THE DRAWINGS

FIG. 1 depicts lowered lymphocyte count after 24 hours (<1 number of lymphocytes $10^3/\mu L$ blood) by Compound 4.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 8, and some intermediates' and reagents' names used in the examples were generated with software such as Chem Bio Draw Ultra version 12.0 or Auto Nom 2000 from MDL ISIS Draw 2.5 SP1 or from a commercial supplier catalog such as Sigma-Aldrich.

In general, characterization of the compounds is performed using NMR spectra which were recorded on 300 and/or 600 MHz Varian and acquired at room temperature. Chemical shifts were given in ppm referenced either to internal TMS or to the solvent signal. Coupling constant J reported in Hz, hertz.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures. Usually the compounds of the invention were purified by column chromatography (Auto-column) on a Teledyne-ISCO CombiFlash with a silica gel column, unless noted otherwise.

The following abbreviations are used in the examples:

| | |
|---|---|
| s, m, h, d | second, minute, hour, day |
| $CH_3CN$ | acetonitrile |
| PSI | pound per square inch |
| DCM | dichloromethane |
| DMF | N,N-dimethylformamide |
| NaOH | sodium hydroxide |
| MeOH | methanol |
| $CD_3OD$ | deuterated methanol |
| $NH_3$ | ammonia |
| HCl | hydrochloric acid |
| $Na_2SO_4$ | sodium sulfate |
| RT or rt | room temperature |
| $MgSO_4$ | magnesium sulfate |
| EtOAc | ethyl acetate |
| $CDCl_3$ | deuterated chloroform |
| $DMSO\text{-}d_6$ | deuterated dimethyl sulfoxide |
| Auto-column | automated flash liquid chromatography |
| TFA | trifluoroacetic acid |
| THF | tetrahydrofuran |
| M | molar |
| $PdCl_2(PPh_3)_2$ | bis(triphenylphosphine)palladium(II) chloride |
| AcOH | acetic acid |
| $K_2CO_3$ | potassium carbonate |
| NaCl | sodium chloride |
| $CHCl_3$ | chloroform |
| HATU | (O-(7-azabenzotriazol-1-yl)-N,N,N',N'-tetramethyluronium hexafluorophosphate) |

Those skilled in the art will be routinely able to modify and/or adapt the following procedures to synthesize any compound of the invention covered by Formula I.

Example 1

Intermediate 1

2-bromo-4-nitro-1-((5-phenylpentyl)oxy)benzene

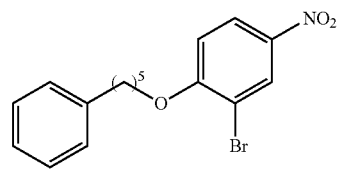

A mixture of 2-bromo-4-nitrophenol (CAS 5847-59-6) (2.05 g, 9.4 mmol), (5-bromopentyl)benzene (CAS 14469-83-1) (2.41 g, 10.6 mmol) and $K_2CO_3$ (3.5 g, 19.1 mmol) was dissolved in DMF (20 mL). The reaction mixture was heated at 100° C. for ~18 h. The mixture was diluted with hexanes: EtOAc (1:1) (~200 mL) and washed with $H_2O$ (3×). The organic solution was dried over $MgSO_4$, filtered, and concentrated onto silica gel under vacuum. Auto-column (9.5 hexanes: 0.5 EtOAc) gave Intermediate 1 as a white solid 1.91 g (56%).

Example 2

Intermediate 2

2-[5-nitro-2-(5-phenyl-pentyloxy)-phenyl]-thiophene

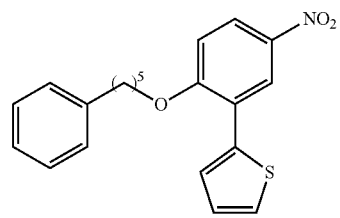

A mixture of Intermediate 1 (1.91 g, 5.25 mmol), tributyl-thiophen-2-yl-stannane (CAS 54663-78-4) (3.4 mL, 10.7 mmol) and $PdCl_2(PPh_3)_2$ (0.55 g, 15 mol %) in DMF (12 mL) was reacted under MWI at 160° C. for 15 m. The mixture was cooled to rt and diluted with hexanes:EtOAc (1:1, 200 mL). The mixture was washed with water (3×), dried over $MgSO_4$, filtered and concentrated onto silica gel under vacuum. Auto-column (9.5 hexanes: 0.5 EtOAc) produced Intermediate 2 as an orange solid, 1.10 g (57%).

Example 3

Intermediate 3

4-(5-phenyl-pentyloxy)-3-thiophen-2-yl-phenylamine

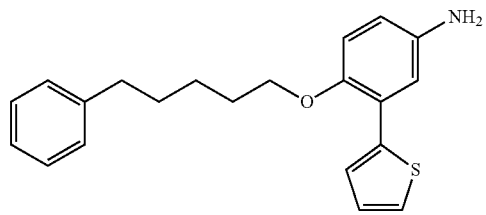 [SMILES: Nc1ccc(OCCCCCc2ccccc2)c(-c2cccs2)c1]

A mixture of iron chips (0.62 g, 11.1 mmol), NH$_4$Cl (0.88 g, 16.4 mmol), water (3.3 mL), and ethanol (10 mL) were heated to reflux for 15 m. This mixture was transferred into a solution of Intermediate 2 (1.0 g, 2.72 mmol) in EtOH (8 mL). The resulting mixture was heated to reflux for 5 h. The mixture was filtered, washed with EtOAc and partitioned between EtOAc and water. The organic layers were dried over MgSO$_4$, filtered and concentrated onto silica gel. Auto-column (7 hexane: 3 EtOAc) gave Intermediate 3, as a tan solid 0.55 g (60%).

Example 4

Intermediate 4

(R)-tert-butyl (3-hydroxy-2-methyl-1-oxo-1-((4-((5-phenylpentyl)oxy)-3-(thiophen-2-yl)phenyl)amino)propan-2-yl)carbamate

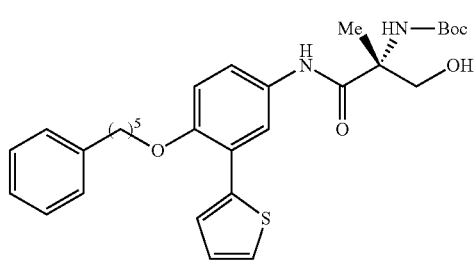

Intermediate 3 (0.30 g, 0.89 mmol), Boc-D-serine (CAS 84311-18-2) (0.25 g, 1.11 mmol), HATU (CAS 148893-10-1) (0.51 g, 1.34 mmol), diisopropylethylamine (CAS 7087-68-5) (0.46 mL) in DMF (20 mL) was reacted at rt for ~18 h. After an aqueous workup and extraction with (hexanes:E-tOAc) the organic layers were combined and concentrated onto silica gel. Auto-column (3% MeOH in CH$_2$Cl$_2$) gave Intermediate 4 0.28 g, (58%).

Example 5

Intermediate 5

2-amino-2-methyl-3-oxo-3-({4-[(5-phenylpentyl)oxy]-3-(2-thienyl)phenyl}amino)propyl dihydrogen phosphate

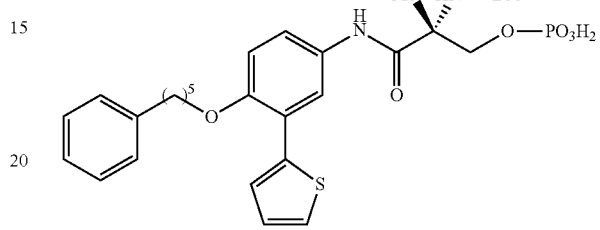

Intermediate 4 (0.28 g, 5.20 mmol), tetrazole (7.0 mL, 3.15 mmol; 0.45 M in CH$_3$CN), and di-tert-butyl diisopropyl-phosphoramidite (0.65 mL, 2.06 mmol) in DMF (5 mL) were stirred at RT for ~18 h. Hydrogen peroxide 35% (0.19 mL, 2.2 mmol) excess was added at 0° C. and the mixture was warmed to RT and stirred for 1 h. The solvent was removed under vacuum and the residue was quenched with sat. Na$_2$S$_2$O$_3$ (10% aq) and extracted with EtOAc. The organic layers were dried over MgSO$_4$, filtered, concentrated onto silica gel under vacuum. Auto-column (6 hexanes: 4 EtOAc) gave Intermediate 5 as a white solid 0.27 g (71%).

Example 6

Compound 1

(2R)-2-amino-2-methyl-3-oxo-3-({4-[(5-phenylpentyl)oxy]-3-(2-thienyl)phenyl}amino)propyl dihydrogen phosphate

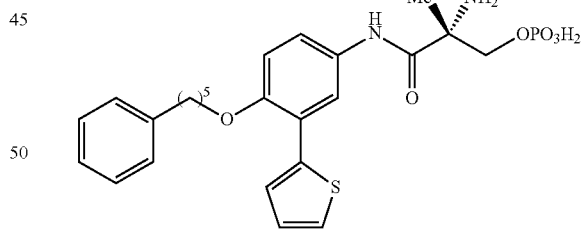

Intermediate 5 was dissolved in CH$_2$Cl$_2$ and reacted with HCl in dioxane. The mixture was reacted for ~18 h at rt. The solvent was removed under vacuum and the crude material was titurated several times with diethyl ether to give Compound 1 as a solid, ~160 mg.

(300 MHz, CD$_3$OD): δ 7.89 (d, J=2.4, 1H), 7.50-7.44 (m, 2H), 7.37 (d, J=5.4, 1H), 7.26-7.21 (m, 2H), 7.17-7.13 (m, 3H), 7.06-7.00 (m, 2H), 4.42 (dd, J=5.1, 11.4, 1H), 4.20 (dd, J=4.8, 11.7, 1H), 4.08 (t, J=6.3, 2H), 2.63 (t, J=7.2, 2H), 1.91-1.84 (m, 2H), 1.74-1.65 (m, 2H), 1.68 (s, 3H), 1.62-1.53 (m, 2H).

Compound 2 prepared from the corresponding starting materials in a similar manner to the procedure described for Compound 1. The results are tabulated below in Table 1.

TABLE 1

Compound 2

| | |
|---|---|
| IUPAC Name | (2S)-2-amino-2-methyl-3-oxo-3-({4-[(5-phenylpentyl)oxy]-3-(2-thienyl)phenyl}amino)propyl dihydrogen phosphate |
| Structure | |
| $^1$H NMR δ (ppm) | (600 MHz, CD$_3$OD/CDCl$_3$) δ: 7.91 (d, J = 2.4, 1H), 7.51 (d, J = 3.0, 1H), 7.45 (dd, J = 2.4, 9.0, 1H), 7.33 (d, J = 4.8, 1H), 7.25 (t, J = 7.8, 2H), 7.18-7.14 (m, 3H), 7.06 (t, J = 4.8, 1H), 6.95 (d, J = 9.0, 1H), 4.27 (dd, J = 5.4, 10.8, 1H), 4.07 (t, J = 6.6, 2H), 3.96 (dd, J = 5.4, 9.6, 1H), 2.65 (t, J = 7.8, 2H), 1.93-1.89 (m, 2H), 1.74-1.68 (m, 2H), 1.61-1.57 (m, 2H), 1.50 (s, 3H). |
| Intermediate(s) starting material(s) | 1, 2 and 3<br>Boc-L-serine |

Example 7

Intermediate 7

2-(2-(benzyloxy)-5-nitrophenylfuran

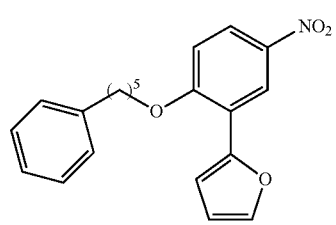

Intermediate 7 was prepared from Intermediate 1 and tributyl-2-furanyl-stannane, in a similar manner to the procedure described in Example 2 for Intermediate 2.

Example 8

Intermediate 8

3-furan-2-yl-4-(5-phenyl-pentyloxy)-phenylamine

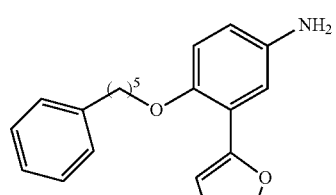

Intermediate 8 was prepared from Intermediate 7 in a similar manner to the procedure described in Example 3 for Intermediate 3.

Example 9

Intermediate 9

{(S)-1-[3-furan-2-yl-4-(5-phenyl-pentyloxy)-phenyl-carbamoyl]-2-hydroxy-ethyl}-carbamic acid benzyl ester

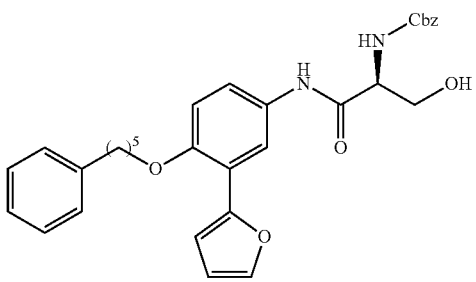

Intermediate 8 (0.98 g, 3.05 mmol), N-carbobenzoxy-L-serine (0.82 g, 3.36 mmol), HATU (2.0 g, 5.1 mmol), and diisopropylethylamine (1.8 mL, 10.3 mmol) in DMF (30 mL)

was allowed to react for ~18 h at RT. Auto column (6 hexanes:4 EtOAc) gave a crude Intermediate 9 as a yellow solid, 1.32 g (80%).

Example 10

Intermediate 10 benzyl [2-({3-(2-furyl)-4-[(5-phenylpentyl)oxy]phenyl}amino)-1-{[(3-oxido-1,5-dihydro-2,4,3-benzodioxaphosphepin-3-yl)oxy]methyl}-2-oxoethyl]carbamate

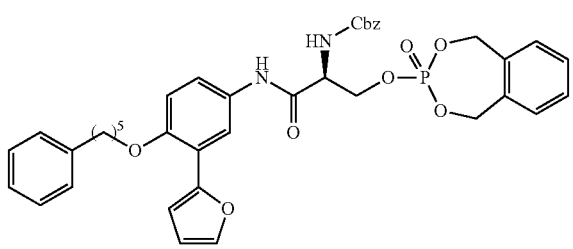

Intermediate 9 (1.32 g, 2.43 mmol), tetrazole (16.2 mL, 7.29 mmol; 0.45 M in CH$_3$CN), and 3-(diethylamino)-1,5-dihydro-2,4,3-benzodioxaphosphepine (CAS 82372-35-8) (0.88 mL, 3.67 mmol) in THF (25 mL) were stirred at RT for ~24 h. Hydrogen peroxide 35% (4.7 mL, 54.6 mmol) excess was added and the mixture was stirred for 1 h. The solvent was removed under vacuum and the residue was quenched with sat. Na$_2$S$_2$O$_3$ and extracted with EtOAc. The organic layers were dried over MgSO$_4$. Auto-column (5 hexanes: 5 EtOAc) gave a crude Intermediate 10 as a yellow oil ~0.86 g.

Example 11

Compound 3

(2S)-2-amino-3-({3-(2-furyl)-4-[(5-phenylpentyl)oxy]phenyl}amino)-3-oxopropyl dihydrogen phosphate

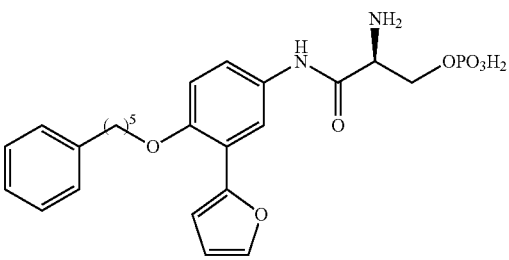

Intermediate 10 (0.86 g, 1.19 mmol) was treated with 10% Pd on C (0.30 g) and hydrogen at 50 psi for 3 h. The mixture was filtered through celite. The filtrate was concentrated onto silica gel and purified with auto-column (gradient 0→100% MeOH in CH$_2$Cl$_2$) to give Compound 3 as a solid ~50 mg.

(300 MHz, DMSO-d$_6$) δ: 8.10 (d, J=2.7, 1H), 7.70 (s, 1H), 7.47 (dd, J=2.1, 8.7, 1H), 7.27-7.14 (m, 6H), 6.99 (d, J=8.7, 1H), 6.85 (d, J=3.0, 1H), 6.54 (dd, J=1.8, 3.6, 1H), 4.02 (t, J=6.3, 2H), 3.98-3.90 (m, 3H), 2.58 (t, J=7.5, 2H), 1.84-1.78 (m, 2H), 1.67-1.62 (m, 2H), 1.52-1.44 (m, 2H).

Compound 4 prepared from Intermediate 3 and the corresponding procedure(s) as described for preparation of Intermediate 10 and in Example 11 for Compound 3. The results are tabulated below in Table 2.

TABLE 2

| | Compound 4 |
|---|---|
| IUPAC Name | (2S)-2-amino-3-oxo-3-({4-[(5-phenylpentyl)oxy]-3-(2-thienyl)phenyl}amino)propyl dihydrogen phosphate |
| Structure | 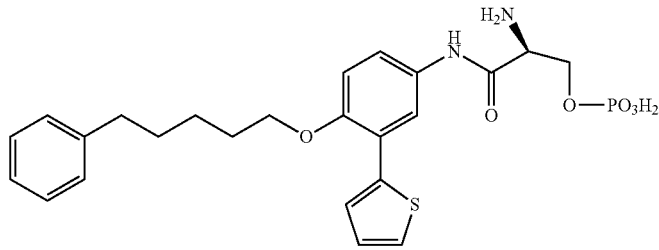 |
| $^1$H NMR δ (ppm) | (600 MHz, CF$_3$C(O)OD) δ: 7.68 (d, J = 3.0, 1H), 7.30-7.28 (m, 1H), 7.25-7.22 (m, 3H), 7.20-7.16 (m, 3H), 7.14 (t, J = 7.2, 1H), 7.10 (d, J = 9.0, 1H), 7.06 (d, J = 3.0, 1H), 5.02-4.97 (m, 2H), 4.80-4.77 (m, 1H), 4.17 (t, J = 6.6, 2H), 2.65 (t, J = 7.2, 2H), 1.96-1.92 (m, 2H), 1.75-1.70 (m, 2H), 1.59-1.56 (m, 2H). |
| Intermediate | 3 |

Biological Examples

In Vitro Assay

Compounds were tested for S1P1 activity using the GTP γ$^{35}$S binding assay. These compounds may be assessed for their ability to activate or block activation of the human S1P1 receptor in cells stably expressing the S1P1 receptor. GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Activity Potency:
S1P1 receptor from GTP γ$^{35}$S: nM, (EC$_{50}$),

TABLE 3

| IUPAC name | S1P1 EC$_{50}$ (nM) |
| --- | --- |
| (2R)-2-amino-2-methyl-3-oxo-3-({4-[(5-phenylpentyl)oxy]-3-(2-thienyl)phenyl}amino)propyl dihydrogen phosphate | 96 |
| (2S)-2-amino-2-methyl-3-oxo-3-({4-[(5-phenylpentyl)oxy]-3-(2-thienyl)phenyl}amino)propyl dihydrogen phosphate | 34 |
| (2S)-2-amino-3-({3-(2-furyl)-4-[(5-phenylpentyl)oxy] phenyl}amino)-3-oxopropyl dihydrogen phosphate | 8 |
| (2S)-2-amino-3-oxo-3-({4-[(5-phenylpentyl)oxy]-3-(2-thienyl)phenyl}amino)propyl dihydrogen phosphate | 3 |

Lymphopenia Assay in Mice

Test drugs are prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

A lymphopenia assay in mice; as previously described, was employed to measure the in vivo blood lymphocyte depletion after dosing with (2S)-2-amino-3-oxo-3-({4-[(5-phenylpentyl)oxy]-3-(2-thienyl)phenyl}amino)propyl dihydrogen phosphate. This S1P1 agonist is useful for S1P-related diseases and exemplified by the lymphopenia in vivo response. Test drug, (2S)-2-amino-3-oxo-3-({4-[(5-phenylpentyl)oxy]-3-(2-thienyl)phenyl}amino)propyl dihydrogen phosphate was prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples were obtained by puncturing the submandibular skin with a Goldenrod animal lancet at different time intervals such as: 24, 48, 72, and 96 h post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). Results are shown in FIG. 1 that depicts lowered lymphocyte count after 24 hours (<1 number of lymphocytes 10$^3$/μL blood).

What is claimed:

1. A method of treating an immunosuppressant disorder associated with the sphingosine-1-phosphate receptor modulation, wherein the immunosuppressant disorder is selected from: rheumatoid arthritis, psoriasis, atherosclerosis, autoimmune uveitis, dry eye, inflammatory bowel diseases, atopic allergy, atopic dermatitis, contact dermatitis, multiple sclerosis, Sjogren's syndrome and organ transplant rejection, in a mammal in need thereof, which comprises administering to a mammal in need thereof, a pharmaceutical composition comprising a therapeutically effective amount of at least one compound represented by Formula I or a pharmaceutically acceptable salt thereof:

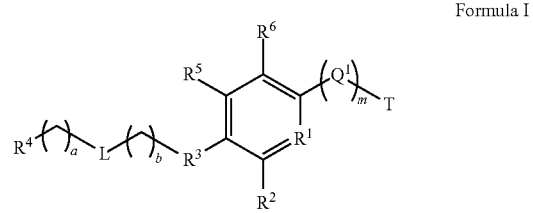

Formula I wherein:

R$^1$ is N or C—R$^9$;

R$^2$ is substituted or unsubstituted heterocycle, C$_{5-8}$ cycloalkenyl or C$_{6-10}$ aryl;

R$^3$ is O, N—R$^{10}$, CH—R$^{11}$, S, —CR$^{12}$=CR$^{13}$—, —C≡C— or —C(O)—;

R$^4$ is H, C$_{5-8}$ cycloalkenyl, C$_{3-8}$ cycloalkyl or substituted or unsubstituted C$_{6-10}$ aryl;

R$^5$ is H, halogen, —OC$_{1-3}$ alkyl, C$_{1-3}$ alkyl or hydroxyl;

R$^6$ is H, halogen, —OC$_{1-3}$ alkyl, C$_{1-3}$ alkyl or hydroxyl;

a is 0, 1, 2, 3 or 4;

b is 0, 1, 2, 3 or 4;

L is CHR$^7$, O, S, NR$^8$ or —C(O)—;

R$^7$ is H, C$_{1-3}$ alkyl, —OC$_{1-3}$ alkyl, halogen, hydroxyl or NR$^9$R$^{10}$;

R$^8$ is H or C$_{1-3}$ alkyl;

R$^9$ is H, halogen or C$_{1-3}$ alkyl;

R$^{10}$ is H or C$_{1-3}$ alkyl;

R$^{11}$ is H or C$_{1-3}$ alkyl;

R$^{12}$ is H or C$_{1-3}$ alkyl;

R$^{13}$ is H or C$_{1-3}$ alkyl;

Q$^1$ is —CR$^{14}$R$^{15}$—;

R$^{14}$ is H, halogen, or C$_{1-3}$ alkyl;

R$^{15}$ is H, halogen, or C$_{1-3}$ alkyl;

m is 0, 1, 2 or 3;

T is —NH—Q², 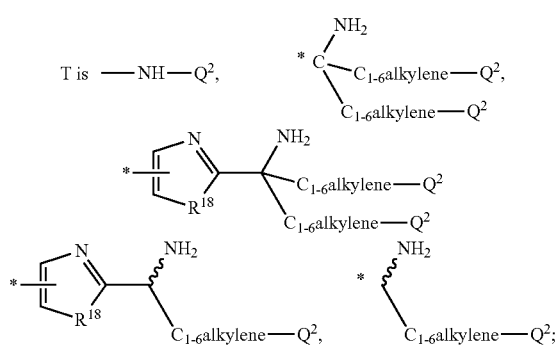

"*" represents the point of attachment to the rest of the molecule;

R¹⁸ is NR⁹, O, or S;

Q² is the same or independently —OPO₃H₂, carboxylic acid, —PO₃H₂, —S(O)₂OH, —P(O)MeOH, —P(O)(H)OH, —OH,

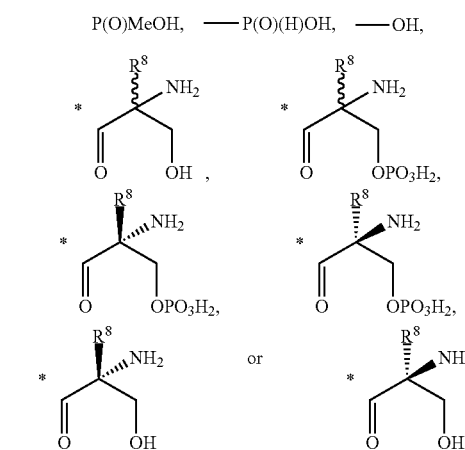

with the proviso that when R³ is O, N—R¹⁰, S, —CR¹²=CR¹³—, —C≡C— or —C(O)— and b is 0 or 1 then L is not O, S, NR⁸ or —C(O)—.

2. The method according to claim 1, wherein said compound is represented by Formula I wherein:

R² is selected from: furan, 2-furyl and 3-furyl derivatives; thiophene, 2-thienyl and 3-thienyl derivatives; pyrrole, oxazole, thiazole, pyrrolidine, pyrroline, imidazole, pyrazole, pyrazoline, isoxazole, isothiazole, pyrazolidine, imidazoline, thiazoline, oxazoline, dihydrothiophene, dihydrofuran, tetrazole, triazole, oxadiazole, 1,2,5-oxadiazole, thiadiazole, 1,2,3-triazole, 1,2,4-triazole, pyrrolidinone, pyrrol-2(3H)-one, imidazolidin-2-one and 1,2,4-triazol-5(4H).

3. The method according to claim 1, wherein said compound is represented by Formula I wherein:

R⁴ is phenyl with ortho, meta and para substitution with groups selected from: fluoro, chloro, bromo, methyl, ethyl, propyl, isopropyl, methoxy, trifluoromethoxy, trifluoromethyl, perfluorinated ethyl, perfluorinated propyl and perfluorinated isopropyl.

4. The method according to claim 1, wherein said compound is represented by Formula I wherein:

R³ is O.

5. The method according to claim 1, wherein said compound is represented by Formula I wherein:
R¹ is N.

6. The method according to claim 1, wherein said compound is represented by Formula I wherein:
R¹ is C—R⁹.

7. The method according to claim 1, wherein said compound is represented by Formula I wherein:
R¹ is C—R⁹;
R² is five-membered substituted or unsubstituted heterocycle;
R³ is O;
R⁴ is substituted or unsubstituted phenyl;
R⁵ is H or halogen;
R⁶ is H or halogen;
a is 1 or 2;
b is 1 or 2;
L is CHR⁷;
R⁷ is H;
R⁹ is H or C₁₋₃ alkyl;
Q¹ is —CR¹⁴R¹⁵—;
R¹⁴ is H;
R¹⁵ is H;
m is 2;

T is —NH—Q², 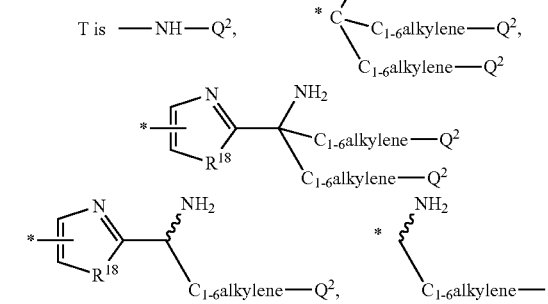

"*" represents the point of attachment to the rest of the molecule;

R¹⁸ is NR⁹;

Q² is the same or independently —OPO₃H₂, carboxylic acid, —PO₃H₂, —P(O)MeOH, —P(O)(H)OH, or —OH.

8. The method according to claim 1, wherein said compound is represented by Formula I wherein:
R¹ is C—R⁹;
R² is five-membered substituted or unsubstituted heterocycle;
R³ is O;
R⁴ is substituted or unsubstituted phenyl;
R⁵ is H or F;
R⁶ is H or F;
a is 1 or 2;
b is 1 or 2;
L is CHR⁷;
R⁷ is H;
R⁹ is H or C₁₋₃ alkyl;
Q¹ is —CR¹⁴R¹⁵—;
R¹⁴ is H;
R¹⁵ is H;
m is 2;

T is —NH—Q², 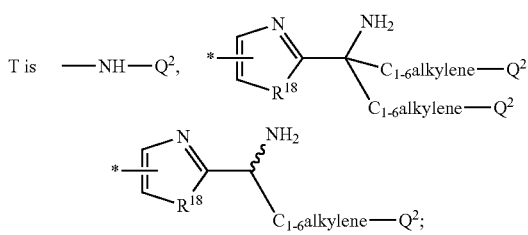

"*" represents the point of attachment to the rest of the molecule;
R¹⁸ is NR⁹;
Q² is the same or independently —OPO₃H₂, carboxylic acid, —PO₃H₂, —P(O)MeOH, —P(O)(H)OH, or —OH.

9. The method according to claim 1, wherein said compound is represented by Formula I wherein:
R¹ is C—R⁹;
R² is five-membered substituted or unsubstituted heterocycle;
R³ is O;
R⁴ is substituted or unsubstituted phenyl;
R⁵ is H or F;
R⁶ is H or F;
a is 1 or 2;
b is 1 or 2;
L is CHR⁷;
R⁷ is H;
R⁹ is H or C$_{1-3}$ alkyl;
Q¹ is —CR¹⁴R¹⁵—;
R¹⁴ is H;
R¹⁵ is H;
m is 2;

T is —NH—Q², 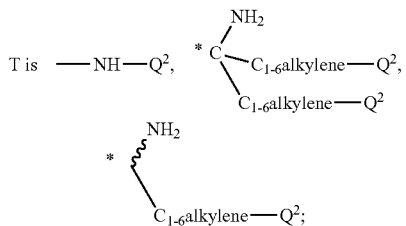

"*" represents the point of attachment to the rest of the molecule;
Q² is the same or independently —OPO₃H₂, carboxylic acid, —PO₃H₂, —P(O)MeOH, —P(O)(H)OH, or —OH.

10. The method according to claim 1, wherein said compound is represented by Formula I wherein:
R¹ is C—R⁹;
R² is substituted or unsubstituted heterocycle;
R³ is O;
R⁴ is substituted or unsubstituted phenyl;
R⁵ is H or halogen;
R⁶ is H or halogen;
a is 2;
b is 2;
L is CHR⁷;
R⁷ is H;
R⁹ is H;
m is 0;
T is —NH-Q², "*" represents the point of attachment to the rest of the molecule;
Q² is the same or independently —OPO₃H₂, carboxylic acid, —PO₃H₂, —S(O)₂OH, —P(O)MeOH, —P(O)(H)OH, —OH

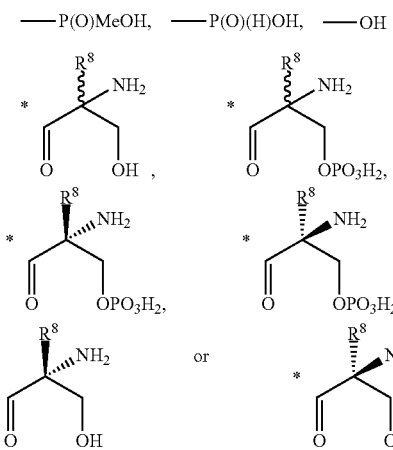

11. The method according to claim 1, wherein said compound is represented by Formula I wherein:
R¹ is C—R⁹;
R² is substituted or unsubstituted heterocycle;
R³ is O;
R⁴ is substituted or unsubstituted phenyl;
R⁵ is H or F;
R⁶ is H or F;
a is 2;
b is 2;
L is CHR⁷;
R⁷ is H;
R⁹ is H;
m is 0;
T is —NH-Q²,
"*" represents the point of attachment to the rest of the molecule;
Q² is the same or independently —OPO₃H₂, carboxylic acid, —PO₃H₂, —S(O)₂OH, —P(O)MeOH, —P(O)(H)OH, —OH, or

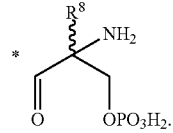

12. The method according to claim 1, wherein said compound is represented by Formula I wherein:
R¹ is C—R⁹;
R² is substituted or unsubstituted heterocycle;
R³ is O;
R⁴ is substituted or unsubstituted phenyl;
R⁵ is H or F;
R⁶ is H or F;
a is 2;
b is 2;
L is CHR⁷;
R⁷ is H;
R⁹ is H;
m is 0;

T is —NH-Q²,
"*" represents the point of attachment to the rest of the molecule;
Q² is the same or independently —OPO₃H₂, carboxylic acid, —PO₃H₂, —S(O)₂OH,

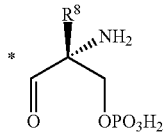 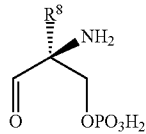

13. The method according to claim 1, wherein said compound is represented by Formula I wherein:
R¹ is C—R⁹;
R² is substituted or unsubstituted heterocycle;
R³ is O;
R⁴ is substituted or unsubstituted phenyl;
R⁵ is H or F;
R⁶ is H or F;
a is 2;
b is 2;
L is CHR⁷;
R⁷ is H;
R⁹ is H;
m is 0;
T is —NH-Q²,
"*" represents the point of attachment to the rest of the molecule;
Q² is the same or independently —OPO₃H₂, carboxylic acid, —PO₃H₂, —S(O)₂OH, —P(O)MeOH, —P(O)(H)OH, —OH, or

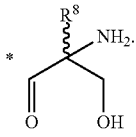

14. The method according to claim 1, wherein said compound is represented by Formula I wherein:
R¹ is C—R⁹;
R² is substituted or unsubstituted heterocycle;
R³ is O;
R⁴ is substituted or unsubstituted phenyl;
R⁵ is H or F;
R⁶ is H or F;
a is 2;
b is 2;
L is CHR⁷;
R⁷ is H;
R⁹ is H;
m is 0;
T is —NH-Q²,
"*" represents the point of attachment to the rest of the molecule;
Q² is the same or independently —OPO₃H₂, carboxylic acid, —PO₃H₂, —S(O)₂OH,

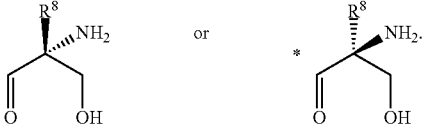

15. The method according to claim 1, wherein the compound represented by Formula I is selected from:
(2R)-2-amino-2-methyl-3-oxo-3-({4-[(5-phenylpentyl)oxy]-3-(2-thienyl)phenyl}amino)propyl dihydrogen phosphate;
(2S)-2-amino-2-methyl-3-oxo-3-({4-[(5-phenylpentyl)oxy]-3-(2-thienyl)phenyl}amino)propyl dihydrogen phosphate;
2-amino-3-hydroxy-2-methyl-N-{4-[(5-phenylpentyl)oxy]-3-(2-thienyl)phenyl}propanamide;
2-amino-3-hydroxy-2-methyl-N-{4-[(5-phenylpentyl)oxy]-3-(2-thienyl)phenyl}propanamide;
(2S)-2-amino-3-({3-(2-furyl)-4-[(5-phenylpentyl)oxy]phenyl}amino)-3-oxopropyl dihydrogen phosphate;
(2S)-2-amino-3-oxo-3-({4-[(5-phenylpentyl)oxy]-3-(2-thienyl)phenyl}amino)propyl dihydrogen phosphate;
2-amino-N-{3-(2-furyl)-4-[(5-phenylpentyl)oxy]phenyl}-3-hydroxypropanamide;
2-amino-3-hydroxy-N-{4-[(5-phenylpentyl)oxy]-3-(2-thienyl)phenyl}propanamide;
2-amino-3-({3-(5-fluoro-2-furyl)-4-[(5-phenylpentyl)oxy]phenyl}amino)-3-oxopropyl dihydrogen phosphate;
2-amino-3-{[4-{[5-(4-fluorophenyl)pentyl]oxy}-3-(2-furyl)phenyl]amino}-3-oxopropyl dihydrogen phosphate;
2-amino-3-({3-(3-furyl)-4-[(5-phenylpentyl)oxy]phenyl}amino)-3-oxopropyl dihydrogen phosphate;
2-amino-3-oxo-3-({4-[(5-phenylpentyl)oxy]-3-(3-thienyl)phenyl}amino)propyl dihydrogen phosphate;
2-amino-3-({6-(2-furyl)-5-[(5-phenylpentyl)oxy]pyridin-2-yl}amino)-3-oxopropyl dihydrogen phosphate;
2-amino-N-{3-(5-fluoro-2-furyl)-4-[(5-phenylpentyl)oxy]phenyl}-3-hydroxypropanamide;
2-amino-N-{3-(5-fluoro-2-furyl)-4-[(5-phenylpentyl)oxy]phenyl}-3-hydroxypropanamide;
2-amino-N-{3-(3-furyl)-4-[(5-phenylpentyl)oxy]phenyl}-3-hydroxypropanamide;
2-amino-3-hydroxy-N-{4-[(5-phenylpentyl)oxy]-3-(3-thienyl)phenyl}propanamide;
2-amino-N-{6-(2-furyl)-5-[(5-phenylpentyl)oxy]pyridin-2-yl}-3-hydroxypropanamide;
2-amino-4-{3-(2-furyl)-4-[(5-phenylpentyl)oxy]phenyl}-2-(hydroxymethyl)butyl dihydrogen phosphate;
2-amino-2-(hydroxymethyl)-4-{4-[(5-phenylpentyl)oxy]-3-(2-thienyl)phenyl}butyl dihydrogen phosphate;
2-amino-4-{3-(5-fluoro-2-furyl)-4-[(5-phenylpentyl)oxy]phenyl}-2-(hydroxymethyl)butyl dihydrogen phosphate;
2-amino-4-[4-{[5-(4-fluorophenyl)pentyl]oxy}-3-(2-furyl)phenyl]-2-(hydroxymethyl)butyl dihydrogen phosphate;
2-amino-4-{3-(3-furyl)-4-[(5-phenylpentyl)oxy]phenyl}-2-(hydroxymethyl)butyl dihydrogen phosphate;
2-amino-2-(hydroxymethyl)-4-{4-[(5-phenylpentyl)oxy]-3-(3-thienyl)phenyl}butyl dihydrogen phosphate;
2-amino-4-{6-(2-furyl)-5-[(5-phenylpentyl)oxy]pyridin-2-yl}-2-(hydroxymethyl)butyl dihydrogen phosphate;

2-amino-2-(2-{3-(2-furyl)-4-[(5-phenylpentyl)oxy] phenyl}ethyl)propane-1,3-diol;
2-amino-2-(2-{4-[(5-phenylpentyl)oxy]-3-(2-thienyl) phenyl}ethyl)propane-1,3-diol;
2-amino-2-(2-{3-(5-fluoro-2-furyl)-4-[(5-phenylpentyl) oxy]phenyl}ethyl)propane-1,3-diol;
2-amino-2-{2-[4-{[5-(4-fluorophenyl)pentyl]oxy}-3-(2-furyl)phenyl]ethyl}propane-1,3-diol;
2-amino-2-(2-{3-(3-furyl)-4-[(5-phenylpentyl)oxy] phenyl}ethyl)propane-1,3-diol;
2-amino-2-(2-{4-[(5-phenylpentyl)oxy]-3-(3-thienyl) phenyl}ethyl)propane-1,3-diol;
2-amino-2-(2-{6-(2-furyl)-5-[(5-phenylpentyl)oxy]pyridin-2-yl}ethyl)propane-1,3-diol;
2-amino-2-(4-{3-(2-furyl)-4-[(5-phenylpentyl)oxy]phenyl}-1H-imidazol-2-yl)ethyl dihydrogen phosphate;
2-amino-2-(4-{4-[(5-phenylpentyl)oxy]-3-(2-thienyl) phenyl}-1H-imidazol-2-yl)ethyl dihydrogen phosphate;
2-amino-2-(4-{3-(5-fluoro-2-furyl)-4-[(5-phenylpentyl) oxy]phenyl}-1H-imidazol-2-yl)ethyl dihydrogen phosphate;
2-amino-2-{4-[4-{[5-(4-fluorophenyl)pentyl]oxy}-3-(2-furyl)phenyl]-1H-imidazol-2-yl}ethyl dihydrogen phosphate;
2-amino-2-(4-{3-(3-furyl)-4-[(5-phenylpentyl)oxy]phenyl}-1H-imidazol-2-yl)ethyl dihydrogen phosphate;
2-amino-2-(4-{4-[(5-phenylpentyl)oxy]-3-(3-thienyl) phenyl}-1H-imidazol-2-yl)ethyl dihydrogen phosphate;
2-amino-2-(4-{6-(2-furyl)-5-[(5-phenylpentyl)oxy]pyridin-2-yl}-1H-imidazol-2-yl)ethyl dihydrogen phosphate;
2-amino-2-(4-{3-(2-furyl)-4-[(5-phenylpentyl)oxy]phenyl}-1H-imidazol-2-yl)ethanol;
2-amino-2-(4-{4-[(5-phenylpentyl)oxy]-3-(2-thienyl) phenyl}-1H-imidazol-2-yl)ethanol;
2-amino-2-(4-{3-(5-fluoro-2-furyl)-4-[(5-phenylpentyl) oxy]phenyl}-1H-imidazol-2-yl)ethanol;
2-amino-2-{4-[4-{[5-(4-fluorophenyl)pentyl]oxy}-3-(2-furyl)phenyl]-1H-imidazol-2-yl}ethanol;
2-amino-2-(4-{3-(3-furyl)-4-[(5-phenylpentyl)oxy]phenyl}-1H-imidazol-2-yl)ethanol;
2-amino-2-(4-{4-[(5-phenylpentyl)oxy]-3-(3-thienyl) phenyl}-1H-imidazol-2-yl)ethanol; and
2-amino-2-(4-{6-(2-furyl)-5-[(5-phenylpentyl)oxy]pyridin-2-yl}-1H-imidazol-2-yl)ethanol.

\* \* \* \* \*

UNITED STATES PATENT AND TRADEMARK OFFICE
CERTIFICATE OF CORRECTION

PATENT NO.       : 8,703,746 B2                           Page 1 of 1
APPLICATION NO.  : 14/071534
DATED            : April 22, 2014
INVENTOR(S)      : Todd M. Heidelbaugh et al.

It is certified that error appears in the above-identified patent and that said Letters Patent is hereby corrected as shown below:

In the Specification

In column 8, line 58, delete "$C_{6-8}$" and insert -- $C_{5-8}$ --, therefor.

In column 8, line 62, delete "$C_{6-8}$" and insert -- $C_{5-8}$ --, therefor.

In column 17, line 53, delete "Stahal&" and insert -- Stahl& --, therefor.

In column 17, line 54, delete "Chemica" and insert -- Chimica --, therefor.

In column 18, line 36, delete "antoimmune" and insert -- autoimmune --, therefor.

In column 18, line 37, delete "dermititis," and insert -- dermatitis, --, therefor.

In column 18, line 59, delete "pemphigold." and insert -- pemphigoid. --, therefor.

In column 19, lines 20-21, delete "antoimmune" and insert -- autoimmune --, therefor.

In column 19, line 22, delete "dermititis," and insert -- dermatitis, --, therefor.

In column 19, line 42, delete "pemphigold." and insert -- pemphigoid. --, therefor.

In column 25, line 2, delete "diasteroisomeric" and insert -- diastereoisomeric --, therefor.

In column 28, line 58, delete "titurated" and insert -- triturated --, therefor.

In column 33, line 10, delete "dithitothreitol" and insert -- dithiothreitol --, therefor.

In column 33, line 15, delete "-adenylylimmidodiphosphate" and
insert -- -adenylylimidodiphosphate --, therefor.

In column 33, line 59, delete "(25)-" and insert -- (2S)- --, therefor.

In column 33, line 63, delete "(25)-" and insert -- (2S)- --, therefor.

Signed and Sealed this
Fourteenth Day of October, 2014

Michelle K. Lee
*Deputy Director of the United States Patent and Trademark Office*